(12) United States Patent
Mujwid et al.

(10) Patent No.: US 7,094,257 B2
(45) Date of Patent: Aug. 22, 2006

(54) EXPANDABLE INTERVERTEBRAL IMPLANT CAGE

(75) Inventors: James R Mujwid, Crystal, MN (US); Ishmael Bentley, Eagan, MN (US)

(73) Assignee: Zimmer Spine, Inc., Austin, TX (US)

( * ) Notice: Subject to any disclaimer, the term of this patent is extended or adjusted under 35 U.S.C. 154(b) by 42 days.

(21) Appl. No.: 10/685,767

(22) Filed: Oct. 14, 2003

(65) Prior Publication Data

US 2004/0162618 A1 Aug. 19, 2004

Related U.S. Application Data

(60) Provisional application No. 60/448,312, filed on Feb. 14, 2003.

(51) Int. Cl.
*A61F 2/44* (2006.01)

(52) U.S. Cl. .................................. 623/17.15

(58) Field of Classification Search ........ 623/17.11–16
See application file for complete search history.

(56) References Cited

U.S. PATENT DOCUMENTS

| | | | |
|---|---|---|---|
| 4,309,777 A | | 1/1982 | Patil |
| 5,026,373 A | * | 6/1991 | Ray et al. ................. 606/61 |
| 5,505,732 A | | 4/1996 | Michelson |
| 5,605,458 A | | 2/1997 | Bailey et al. |
| 5,653,762 A | | 8/1997 | Pisharodi |
| 5,665,122 A | | 9/1997 | Kambin |
| 5,683,463 A | * | 11/1997 | Godefroy et al. ........ 623/17.16 |
| 5,749,916 A | * | 5/1998 | Richelsoph .............. 623/17.16 |
| 5,865,848 A | * | 2/1999 | Baker ...................... 623/17.15 |
| 5,876,457 A | | 3/1999 | Picha et al. |
| 5,888,228 A | * | 3/1999 | Knothe et al. ........... 623/17.16 |
| 5,976,187 A | * | 11/1999 | Richelsoph .............. 623/17.16 |
| 5,980,522 A | * | 11/1999 | Koros et al. ............... 606/61 |
| 6,045,579 A | * | 4/2000 | Hochshuler et al. ..... 623/17.16 |
| 6,059,829 A | * | 5/2000 | Schlapfer et al. ........ 623/17.16 |
| 6,090,143 A | * | 7/2000 | Meriwether et al. ..... 623/17.11 |
| 6,126,689 A | * | 10/2000 | Brett ....................... 623/17.16 |
| 6,159,244 A | * | 12/2000 | Suddaby .................. 623/17.11 |
| 6,174,334 B1 | * | 1/2001 | Suddaby .................. 623/17.11 |
| 6,176,881 B1 | | 1/2001 | Schär et al. |
| 6,183,517 B1 | * | 2/2001 | Suddaby .................. 623/17.16 |
| 6,190,414 B1 | | 2/2001 | Young et al. |
| 6,332,895 B1 | * | 12/2001 | Suddaby .................. 623/17.11 |
| 6,419,705 B1 | * | 7/2002 | Erickson ................. 623/17.16 |
| 6,419,706 B1 | * | 7/2002 | Graf ........................ 623/17.16 |
| 6,436,142 B1 | * | 8/2002 | Paes et al. ............... 623/17.15 |
| 6,443,989 B1 | * | 9/2002 | Jackson .................. 623/17.15 |

(Continued)

FOREIGN PATENT DOCUMENTS

EP 1 080 703 A2 3/2001

(Continued)

*Primary Examiner*—Eduardo C. Robert
*Assistant Examiner*—Annette Reimers
(74) *Attorney, Agent, or Firm*—Wood, Herron & Evans, LLP

(57) ABSTRACT

An expandable intervertebral implant having an external member and an internal member. The implant includes a locking arrangement having a first interlocking teeth structure formed on the external member and a second interlocking teeth structure formed on the internal member. The interlocking teeth structures of the external and internal members have engagement surfaces arranged in a non-perpendicular orientation relative to the direction of implant expansion. The locking arrangement is configured such that walls of the internal member are pulled or flexed toward the walls of the external member when compressive forces are applied to the implant.

21 Claims, 10 Drawing Sheets

U.S. PATENT DOCUMENTS

| | | | |
|---|---|---|---|
| 6,443,990 B1 * | 9/2002 | Aebi et al. | 623/17.16 |
| 6,454,806 B1 * | 9/2002 | Cohen et al. | 623/17.15 |
| 6,454,807 B1 * | 9/2002 | Jackson | 623/17.15 |
| 6,491,724 B1 * | 12/2002 | Ferree | 623/17.11 |
| 6,500,205 B1 * | 12/2002 | Michelson | 623/17.16 |
| 6,520,991 B1 * | 2/2003 | Huene | 623/17.11 |
| 6,562,074 B1 * | 5/2003 | Gerbec et al. | 623/17.15 |
| 6,648,917 B1 * | 11/2003 | Gerbec et al. | 623/17.11 |
| 6,685,742 B1 * | 2/2004 | Jackson | 623/17.11 |
| 6,716,247 B1 * | 4/2004 | Michelson | 623/17.16 |
| 6,723,126 B1 * | 4/2004 | Berry | 623/17.11 |
| 6,773,460 B1 * | 8/2004 | Jackson | 623/17.15 |
| 6,814,756 B1 * | 11/2004 | Michelson | 623/17.11 |
| 6,821,298 B1 * | 11/2004 | Jackson | 623/17.15 |

FOREIGN PATENT DOCUMENTS

| | | |
|---|---|---|
| EP | 1188424 | 8/2001 |
| EP | 1 188 424 A1 | 3/2002 |
| EP | 1080703 | 8/2002 |
| FR | 2 817 463 A1 | 6/2002 |
| FR | 2817463 | 6/2002 |
| WO | WO03/032812 | 10/2002 |
| WO | WO 03/032812 A2 | 4/2003 |

* cited by examiner

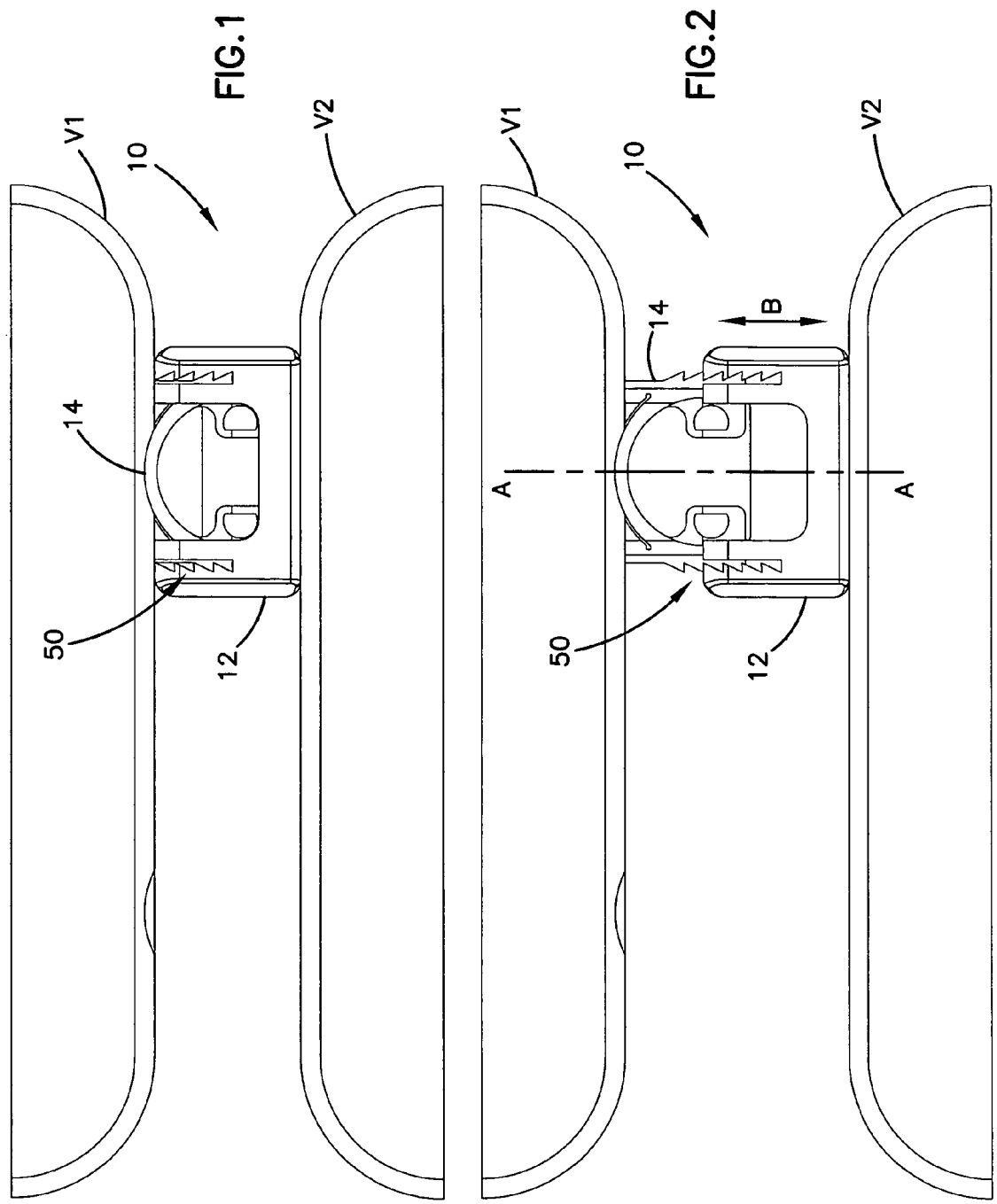

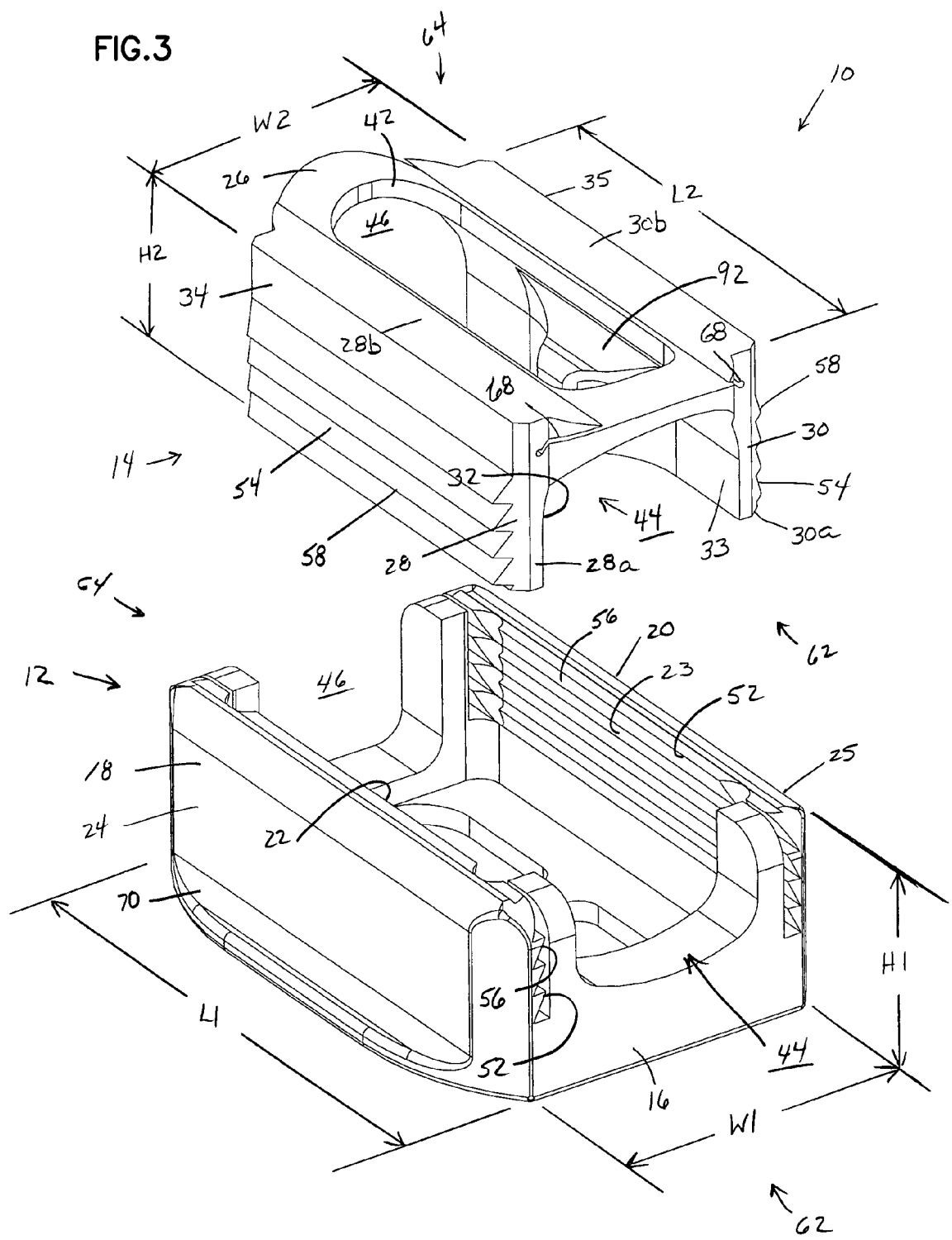

FIG. 5
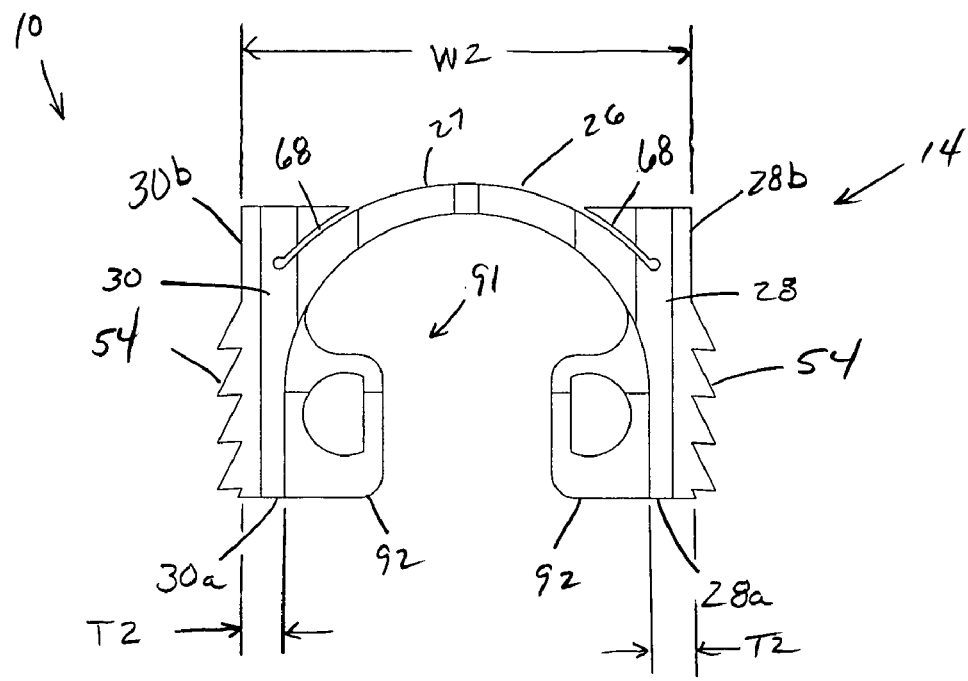
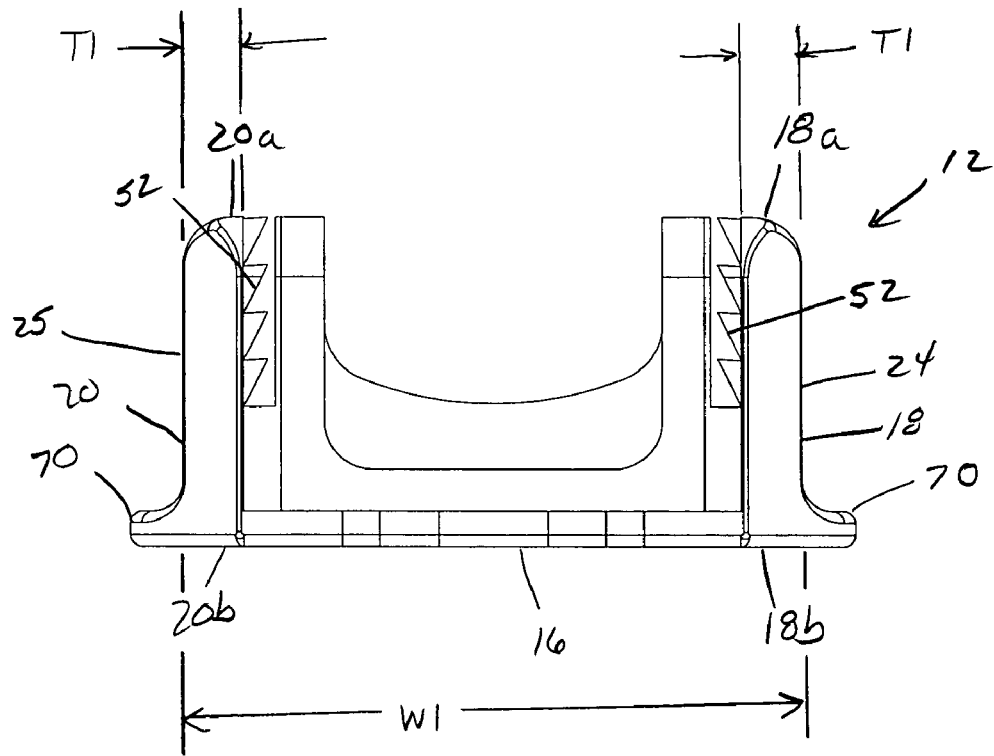

FIG.10
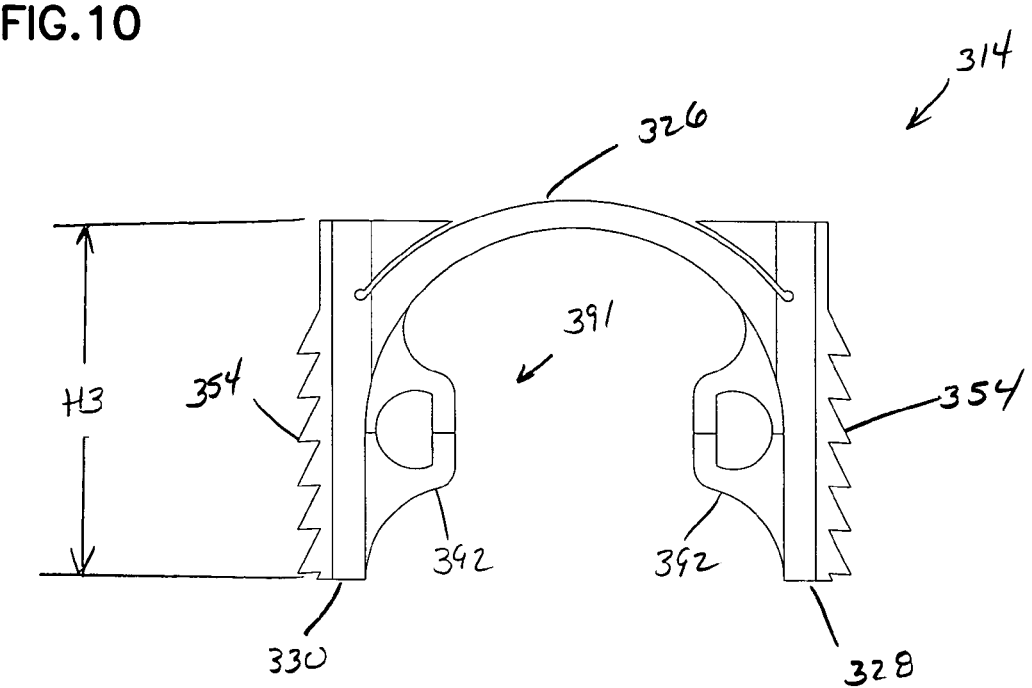
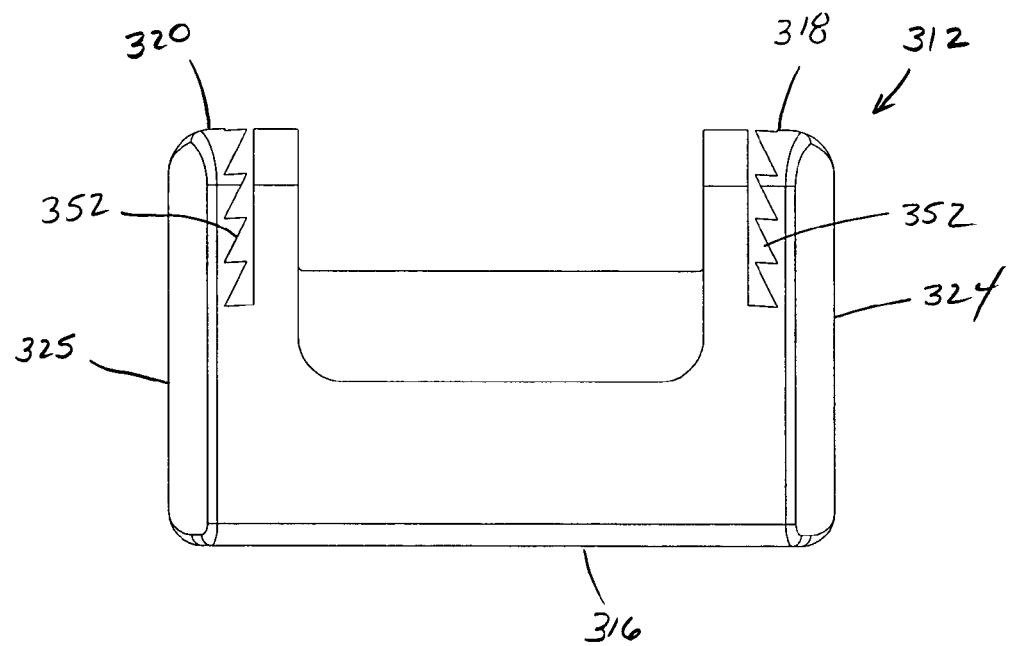

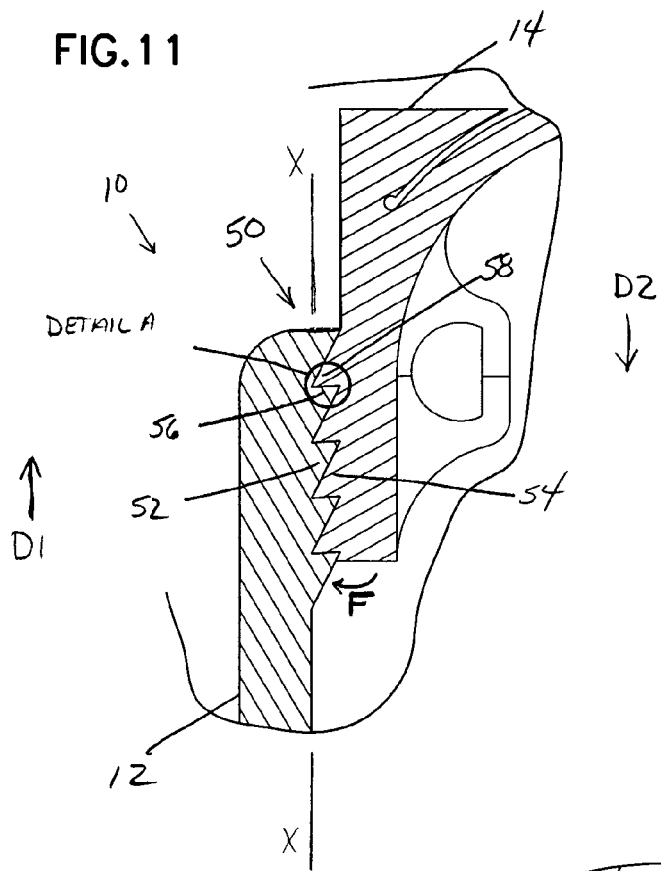
FIG.11
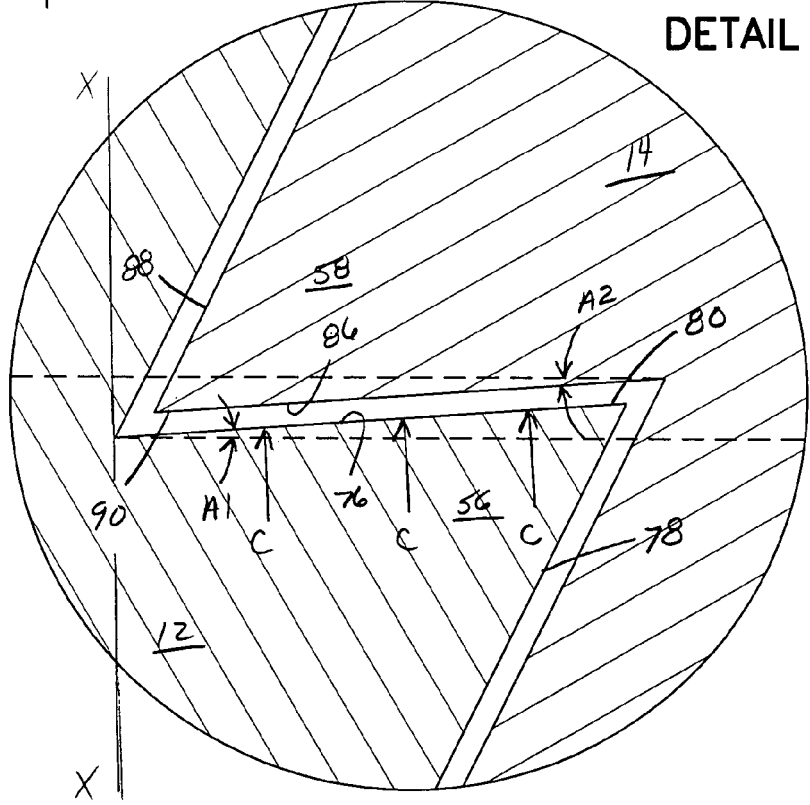
FIG.12 DETAIL A

EXPANDABLE INTERVERTEBRAL IMPLANT CAGE

CROSS-REFERENCE TO RELATED APPLICATIONS

This application claims the benefit of U.S. Provisional Application No. 60/448,312, filed on Feb. 14, 2003, which application is herein incorporated by reference.

TECHNICAL FIELD

This disclosure relates generally to methods and devices for stabilizing adjacent vertebral elements. More particularly, this disclosure relates to an expandable intervertebral implant.

BACKGROUND

A wide variety of configurations of intervertebral implants have been utilized for stabilizing adjacent vertebral elements and facilitating the development of bone union between the vertebral elements. In some configurations, the intervertebral implants are not adjustable by the surgeon during the surgical procedure. Therefore, the surgeon must choose the size that most closely matches the desired height, length and width dimensions, and then make the implant fit. Because these implants are of a predetermined size and shape, the implant site must correspond to the implant configuration. This can require extensive site preparation to complete implantation. Extensive site preparation can compromise the success of the implantation procedure by causing excessive damage to the receiving vertebral elements. In addition, procedures requiring extensive site preparation can result in relatively long surgeries that may increase patient risk.

To address this problem more recent invertebral implants have been designed to expand from a first height to a second height. One such invertebral implant is described in U.S. Pat. No. 6,174,334. This implant includes a pair of shells that when assembled form an implant assembly. Teeth are formed on each shell so that the shells can be unidirectionally spread apart. Each tooth has a ramping surface that is oblique to the line of relative movement of the shells. The ramping surface meets an abutment surface that is perpendicular to the line of relative movement. In other words, each of the teeth formed on the shells has a surface that is 90 degrees relative to the direction in which the shells are spread apart from one another.

It can be understood that as the implant is spread apart, the teeth of the shells ratchet against one another. This ratcheting action causes the lateral walls of the shells to displace laterally. This lateral displacement can cause mechanical stress to a degree at which the shell can experience plastic deformation. If plastic deformation occurs, the two shells of the implant assembly will not interact optimally.

In general, improvement has been sought with respect to such assemblies and systems, generally to provide an expandable implant assembly while maintaining the structural integrity and function of the implant assembly in the event plastic deformation occurs.

SUMMARY

In one aspect, the present disclosure relates to an expandable invertebral implant including first and second members configured to expand between a first position and a second position along an expansion axis of the implant. The implant includes an engagement structure disposed between the first and second members of the implant. The engagement structure has at least one engaging surface having a non-perpendicular orientation relative to the expansion axis of the implant.

In another aspect, the present disclosure relates to an intervertebral implant having external and internal members. Each of the external and internal members includes interlocking teeth structure. The engagement surfaces are arranged in a non-perpendicular orientation relative to the direction of implant expansion. In still another aspect, the interlocking teeth structure of the external and internal members include engagement surfaces, the engagement surfaces being arranged in a non-perpendicular orientation relative to a first wall of each of the external and internal members.

In yet another aspect, the present disclosure relates to an expandable intervertebral implant including external and internal members. The implant also includes a locking arrangement configured to lock the implant in an expanded position. The locking arrangement includes a first configuration of teeth formed on the external member and a second configuration of teeth formed on the internal member. The first configuration of teeth are raked in an upwardly direction and the second configuration of teeth are raked in a downwardly direction.

Yet in another aspect, the present disclosure relates to an expandable intervertebral implant having first and second members, and an interlocking structure formed on each of the first and second members. The interlocking structure is configured to flex the walls of the second member toward the walls of the first member when compressive forces are applied to the first and second members.

A variety of aspects of the invention are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are exemplary and explanatory only, and are not restrictive of the claimed invention.

BRIEF DESCRIPTION OF THE DRAWINGS

FIG. 1 is front elevational view of one embodiment of an expandable intervertebral implant according to the principles of the present disclosure, the implant is shown in a non-expanded position;

FIG. 2 is a front elevational view of the implant of FIG. 1, shown in an expanded position;

FIG. 3 is an exploded, rear perspective view of one embodiment of an expandable intervertebral implant, according to the principles of the present disclosure;

FIG. 5 is a front elevational view of the implant of FIG. 4;

FIG. 10 is a front elevational view of the implant of FIG. 9;

FIG. 11 is an enlarged, partial, front elevational view of an implant according the principles of the present disclosure; and FIG. 12 is a detailed view of FIG. 11.

DETAILED DESCRIPTION

Figure 4:
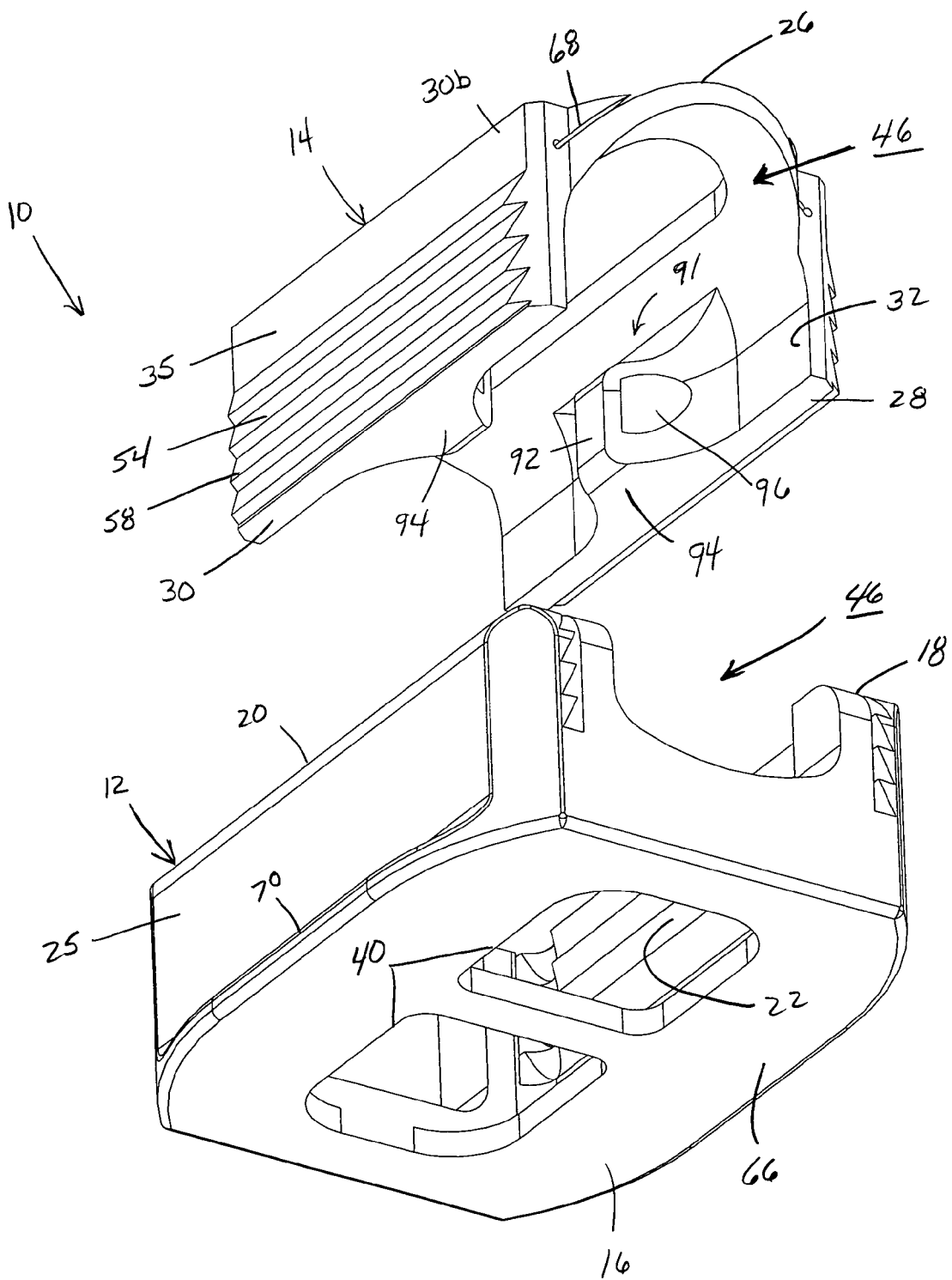
FIG. 4 is an exploded front perspective view of the implant of FIG. 3.

Reference will now be made in detail to exemplary aspects of the present disclosure that are illustrated in the accompanying drawings. Wherever possible, the same reference numbers will be used throughout the drawings to refer to the same or like parts.

Referring to FIGS. 1 and 2, an expandable intervertebral implant 10 is shown, according to the principles of the present disclosure. The implant 10 in FIG. 1 is shown inserted between two vertebral elements V1, V2 in a non-expanded configuration. In FIG. 2, the implant 10 is shown in an expanded configuration. The implant 10 generally includes a first external member 12 and a second internal member 14. The implant also includes an engagement structure or locking arrangement 50 that permits linear expansion in a direction represented by arrow B in FIG. 2. The intervertebral implant 10 is expanded from a first height to a selected second height, and secured at the selected second height by the engagement structure or locking arrangement 50. It is to be understood that the implant 10 is configured to permit expansion to, and be secured at, a variety of selected second heights by incrementally expanding or ratcheting the implant along an axis of expansion A—A. As will be described hereinafter, the implant is also configured to permit linear retraction from the selected second height. The direction of the linear expansion and linear retraction are of the same direction, as represented by arrow B.

The internal and external members 12, 14 of the implant 10 can be machined and/or molded to provide the features herein disclosed. The members 12, 14 may be made of the same material, or different materials. Representative materials typically include biocompatible materials such as stainless steel, ceramics, graphite, carbon fiber materials, and various plastics and composites of the foregoing. In the preferred embodiment, the internal and external members 12, 14 are made of titanium.

Referring now to FIGS. 3–5, a first embodiment of the implant 10 is illustrated. The first external member 12 of the implant 10 generally includes a base portion 16, and first and second external walls 18, 20. The first and second external walls 18, 20 each have a free end 18a, 20a and an attached end 18b, 20b (FIG. 5). The attached ends 18b, 20b are connected to the base portion 16, and the free ends 18a, 20a extend from the base portion 16 in a generally perpendicular orientation. Each of the first and second walls 18, 20 includes an inside wall surface 22, 23 and an outside wall surface 24, 25 (FIG. 3).

In the embodiment shown in FIGS. 3–5, a ledge structure 70 is formed on each side of the implant 10. In use, compressive forces between the vertebral elements V1, V2, which are consequently exerted on the implant, can be significant. The ledge structures 70 provide added stability to the implant 10 by increasing the contact surface area 66 (FIG. 4) of the base portion 16 adjacent to the vertebral element (V2). The ledge structure 70 stabilizes the implant by more widely distributing the compressive loads across the increased contact surface area 66. In the illustrated embodiment, the ledge structures 70 are formed on the external member 12 adjacent to the base portion 16. The ledge structures 70 extend generally from a first end 62 (FIG. 3) of the implant 10 to a second end 64, and project outwardly from the external member 12. A variety of structural configurations that provide added stability to the implant can be used.

The external member 12 has a width W1, a height H1, and a length L1. The width W1 extends between the outside wall surfaces 24, 25 of the first and second walls 18, 20. The width W1 is preferably between 0.3 and 0.7 inches; more preferably the width W1 is between 0.4 and 0.6 inches; and most preferably the width W1 is about 0.5 inches. The height H1 of external member 12 extends from the base portion 16 to the free ends 18a, 20a, of the walls 18, 20. The height H1 is preferably between 0.2 and 0.5 inches; more preferably the height H1 is between 0.2 and 0.4 inches; and most preferably the height is about 0.3 inches. The length L1 of the external member extends generally from the first end 62 of the implant to the second end 64 of the implant. The length L1 of the external member is preferably between 0.5 and 1.2 inches; more preferably the length L1 is between 0.7 and 0.9 inches; and most preferably the length L1 is about 0.8 inches.

The second internal member 14 of the implant 10 generally includes a base portion 26, and first and second internal walls 28, 30. The first and second internal walls 28, 30 each have a free end 28a, 30a and an attached end 28b, 30b (FIG. 3). The attached ends 28b, 30b are connected to the base portion 26, and the free ends 28a, 30a extend from the base portion 26 in a generally perpendicular orientation. Each of the first and second walls 28, 30 include an inside wall surface 32, 33 and an outside wall surface 34, 35.

As shown in FIGS. 4 and 5, the implant 10 includes an implant handling arrangement 91. The implant handling arrangement 91 is configured so that the implant 10 can be handled and manipulated by a surgical tool (not shown) during a surgical procedure. The implant handling structure 92 of the illustrated embodiment is located on the internal member 14 and includes implant handling structures 92 formed on the inside walls surfaces 32, 33 of the first and second walls 28, 30. The handling structures 92 include a projection 94 that projects inward towards the opposing wall 28 or 30. A hole 96 is formed in the projection 94 and is configured to receive an end of a surgical tool, for example. Example instrument embodiments that can be used with the present implants are described in a U.S. application entitled INSTRUMENTS FOR USE WITH IMPLANTS, AND METHODS, U.S. patent application Ser. No. 10/685,768, being filed concurrently herewith; which application is incorporated herein by reference.

The internal member 14 has a width W2, a height H2, and a length L2. The width W2 extends between the outside wall surfaces 34, 35 of the first and second walls 28, 30. The width W2 is preferably between 0.2 and 0.6 inches; more preferably the width W2 is between 0.3 and 0.5 inches; most preferably the width W2 is about 0.4 inches. The height H2 of internal member 14 extends from the base portion 26 to the free ends 28a, 30a of the walls 28, 30. The height H2 is preferably between 0.2 and 0.5 inches; more preferably the height H2 is between 0.2 and 0.4 inches; most preferably the height is about 0.3 inches. The length L2 of the implant extends generally from the first end 62 of the implant to the second end 64 of the implant. The length L2 is preferably between 0.5 and 1.2 inches; more preferably the length L2 is between 0.7 and 0.9 inches; most preferably the length L2 is about 0.8 inches.

In the illustrated embodiment, the external and internal members 12, 14 are configured to interconnect in corresponding relation to one another. In particular, the external walls 18, 20 of the external member 12 are configured and sized for receipt of the internal walls 28, 30 of the internal member 14. In particular, the width W2 of the internal member 14, defined by the outside wall surfaces 34, 35, is configured to interact with the inside wall surfaces 22, 23 of the external member 12. It is contemplated that in an alternative arrangement, the walls of the internal member 14 can be sized and configured such that the inside wall surfaces 32, 33 of the internal member 14 interact with the outside wall surfaces 24, 25 of the external member 12.

Referring to FIG. 5, the external member 12 is configured to be a rigid structure or construction. That is, the first and second walls 18, 20 of the external member 12 are configured to reduce or eliminate flexure of the walls 18, 20 during implant expansion. In particular, the first and second walls 18, 20 of the external member 12 have a thickness T1. The thickness T1 is design to provide rigidity to the external member 12 so that the walls 18, 20 do not laterally displace or flex.

In the context of the external member, what is meant by flex or flexure is the outward movement and returning inward movement of the free ends of the walls, about the attached ends, as the implant 10 is incrementally expanded or ratcheted from the first non-expanded height to the second expanded height (FIGS. 1 and 2). In the context of the internal member, what is meant by flexure is the inward movement and returning outward movement of the free ends of the walls, about the attached ends, as the implant 10 is incrementally expanded from the first non-expanded height to the second expanded height.

In contrast to the rigid construction of the external member 12, the internal member 14 is configured to be a flexible structure or construction. That is, the first and second walls 28, 30 of the internal member 14 are configured to allow or permit flexure of the walls 28, 30 during implant expansion. The flexible construction of the internal member 14 is provided in two ways.

One, the first and second walls 28, 30 of the internal member 14 have a thickness T2. The thickness T2 is less than the thickness T1 of the external member's walls, and is designed to permit lateral displacement or flexure during ratcheting expansion of the implant 10.

Two, the internal member 14 includes slots 68 (FIGS. 3 and 5) formed adjacent to the attached ends 28b, 30b of the walls 28, 30 and the base portion 26. In the illustrated embodiment, the slots 68 have an arcuate shape (FIG. 5) extending from a curvature or curved nose segment 27 of the base portion 26. Preferably the slots 68 extend along the length L2 of the internal member 14 from the first end 62 of the implant to the second end 64 of the implant (FIG. 3). The slots 68 provide a flexible joint that is designed to permit lateral displacement or flexure of the first and second internal walls 28, 30 during expansion of the implant 10.

When the internal and external members 12, 14 are assembled, the base portion and walls 16, 18, and 20 of the first member 12 and the base portion and walls 26, 28, and 30 of the internal member 14 form an opening 44 at the first end 62 of the implant 10 (FIG. 3). Likewise, an opening 46 is formed at the second end 64 of the implant 10. As will be described hereinafter, tools can be inserted within the openings 44, 46 to grasp or manipulate the implant 10 during a surgical procedure. In addition, the openings 44, 46 provide an access to the interior area of the implant. When the implant 10 has been inserted and expanded between two vertebral elements V1, V2 (FIG. 2), bone growth material can be packed within the interior area of the implant through either opening 44, 46.

Referring to FIG. 3, the base portion 26 of the internal member 14 includes an aperture or window 42. The window 42 is provided to encourage bone growth through the implant and between the vertebral elements V1, V2 (FIGS. 1 and 2). In the illustrated embodiment, the window 42 is centrally located in the base portion 26 and has a generally oval shape. Referring to FIG. 4, the base portion 16 of the external member 12 also includes structure to encourage bone growth through the implant and between the vertebral elements V1, V2 (FIGS. 1 and 2). In the illustrated embodiment, the base 16 includes a pair of windows 40 centrally located within the base portion 16. It is contemplated that the implant 10 can include other window configurations having more or less windows of other shapes configured to encourage interlocking bone growth between the vertebral elements.

The engagement structure or locking arrangement 50 (FIGS. 1 and 2) of the implant 10 includes a first interlocking teeth structure 52 (FIGS. 3–5) formed on the first and second walls 18, 20 of the external member 12, and a corresponding second interlocking teeth structure 54 formed on the first and second walls 28, 30 of the internal member 14.

The first interlocking teeth structure 52 of the locking arrangement 50 includes a first configuration of teeth 56 located on the inside wall surfaces 22, 23 of the external member 12; the second interlocking teeth structure 54 of the locking arrangement 50 includes a second configuration of teeth 58 located on the outside wall surfaces 34, 35 of the internal member 14.

Referring now to FIGS. 11 and 12, an enlarged partial view of the implant 10 and a detail view of the locking arrangement 50 are illustrated. As shown in FIG. 12, each of the teeth of the first configuration of teeth 56 includes an engagement surface 76 and an adjacent surface 78. Similarly, each of the teeth in the second configuration 58 includes an engagement surface 86 and an adjacent surface 88. The engagement surfaces 76, 86 meet the adjacent surface 78, 88 at a tip 80, 90, respectively.

The first configuration of teeth 56 of the external member 12 is raked in a direction opposite to the base portion 16 (FIG. 5) of the external member 12. Likewise the second configuration of teeth 58 of the internal member 14 is raked in a direction opposite to the base portion 26 (FIG. 5) of the internal member 14. When the members 12, 14 are assembled together, the first configuration of teeth 56 of the external member 12 are raked in a first upwardly direction, as shown by arrow D1 in FIG. 11; and the second configuration of the teeth 58 of the internal member 14 are raked in a second downwardly direction, as shown by arrow D2. What is meant by "raked" is that the teeth have a rake angle; in particular, the engagement surfaces 76, 86 of the configurations of teeth 56, 58 incline from a perpendicular plane (represented by dashed lines) relative to a plane X—X of the walls of the member 12, 14. In other words, the engagement surfaces 76, 86 are arranged in a non-perpendicular orientation relative to the walls of the external and internal members, and relative to the direction of implant expansion (represent by arrow B in FIG. 2).

Referring to FIG. 11, the engagement surfaces 76 of the first configuration of teeth 56 are raked or oriented at an angle A1 (relative to perpendicular as illustrated by the dash line). In the preferred embodiment, the angle A1 is preferably between one degree and eight degrees, more preferably about four degrees. Likewise, the engagement surfaces 86 of the second configuration of teeth 58 are oriented at an angle A2 (relative to perpendicular as illustrated by the dash line). In the preferred embodiment, the angle A2 is preferably between one degree and eight degrees, more preferably about 4 degrees relative to horizontal. In alternative arrangement, only a portion of the tooth may be raked or oriented an angle relative to the walls. That is, the teeth 56, 58 can have a perpendicular portion and an angled portion configured in accord with the principles disclosed.

In other words, the engagement surfaces 76 of the first interlocking teeth structure 52 formed on the external member 12 is preferably angled between 91 degrees and 98 degrees relative to the inside wall surfaces 22, 23 of the walls 18, 20 of the external member; more preferably approximately 94 degrees relative to the inside wall surfaces. Likewise, the engagement surfaces 86 of the second interlocking teeth structure 54 formed on the internal member 14 is preferably angled between 91 degrees and 98 degrees relative to the outside wall surfaces 34, 35 of the walls 38, 30 of the internal member; more preferably approximately 94 degrees relative to the outside wall surfaces.

The rake angle design of the implant 10 maintains the structural integrity and function of the implant 10 in the event plastic deformation occurs during implant expansion. In particular, the first and second interlocking teeth structures 52, 54 are designed such that the walls 28, 30 of the internal member 14 flex outward toward the walls of the external member 12 (represented by arrow F in FIG. 11) when compressive forces are applied to the implant. More specifically, the external member 12 is a rigid construction designed to reduce or eliminate flexure of the walls 18, 20. Thus, the compressive force C (FIG. 12) from the vertebral element V2 is transferred through the external member 12 to the engagement surfaces 86 of the internal member 14. The rake angle configuration of the engagement surfaces 76, 86 of the interlocking teeth structures 52, 54 transfers a component of the compressive forces C at an angle perpendicular to the engagement surface 86 (represented by arrow C). Because the internal member 14 has a flexible construction designed to permit flexure of the walls 28, 30, the internal walls 28, 30 of the internal member 14 flex in the direction of the compressive force C, i.e. toward the walls 18, 20 of the rigidly constructed external member 12.

This design is advantageous in that expansion of the implant is accommodated by the flexible construction of the internal member 14. Yet, the expansion can cause mechanical stress and fatigue in the structure of the internal member by action of the incremental ratcheting of the locking arrangement 50. In some instances, the mechanical stress can rise to a degree at which plastic deformation occurs. If plastic deformation occurs in a traditional implant assembly, the implant will not perform or interact optimally.

The raked angle configuration of the present implant 10 maintains the structural integrity and function of the implant, even if plastic deformation occurs. In particular, the walls 28, 30 of the internal member 14 are drawn or flexed outward toward the external member 12 by compressive forces C. This pulling or flexing of the walls 28, 30 functions to maintain the walls 28, 30 in the generally perpendicular orientation relative to the base 26, despite any deformation experienced during ratcheting expansion.

Figure 6:
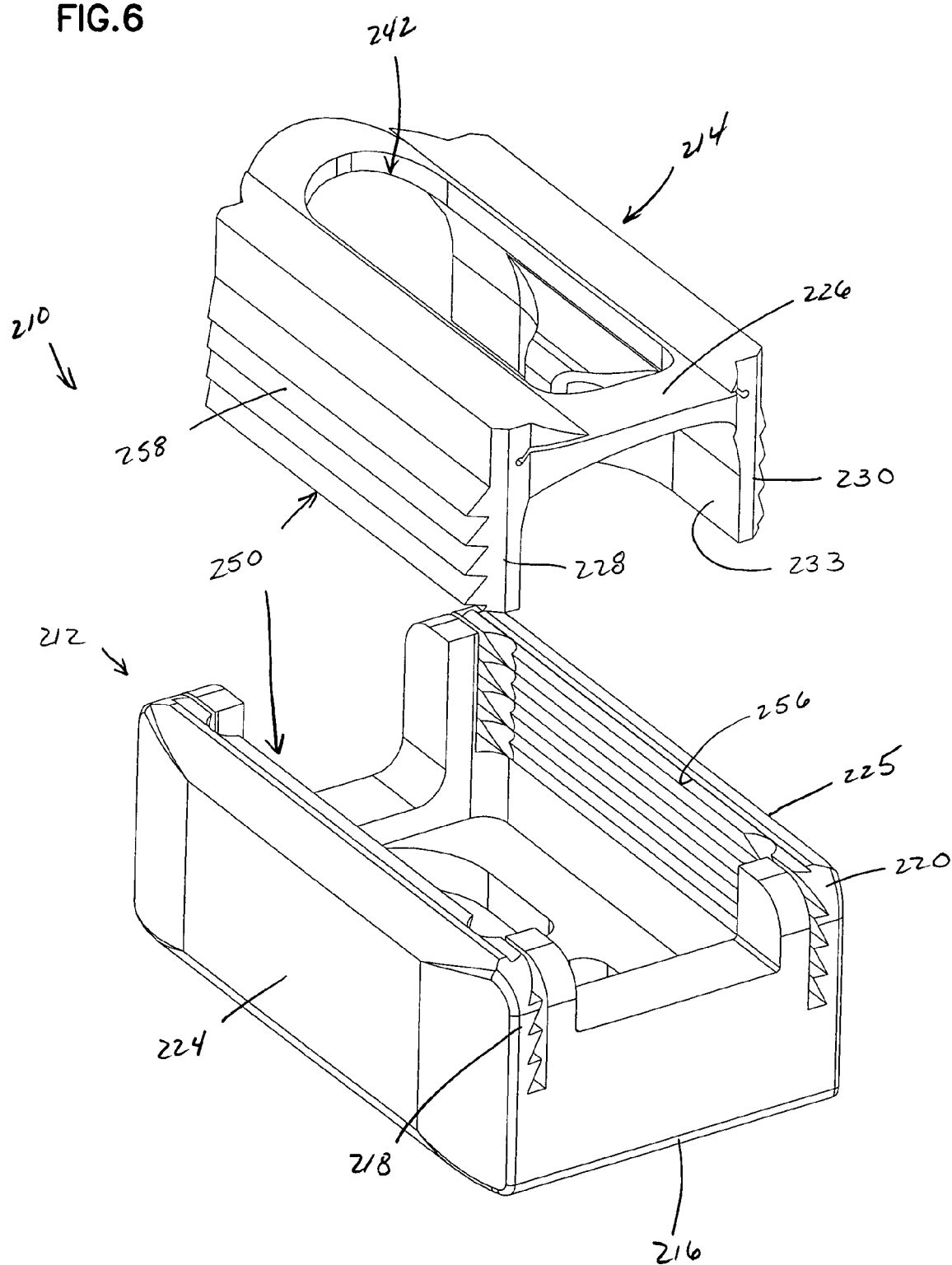
FIG. 6 is an exploded rear perspective view of an alternative embodiment of an expandable intervertebral implant, according to the principles of the present disclosure.
Figure 7:
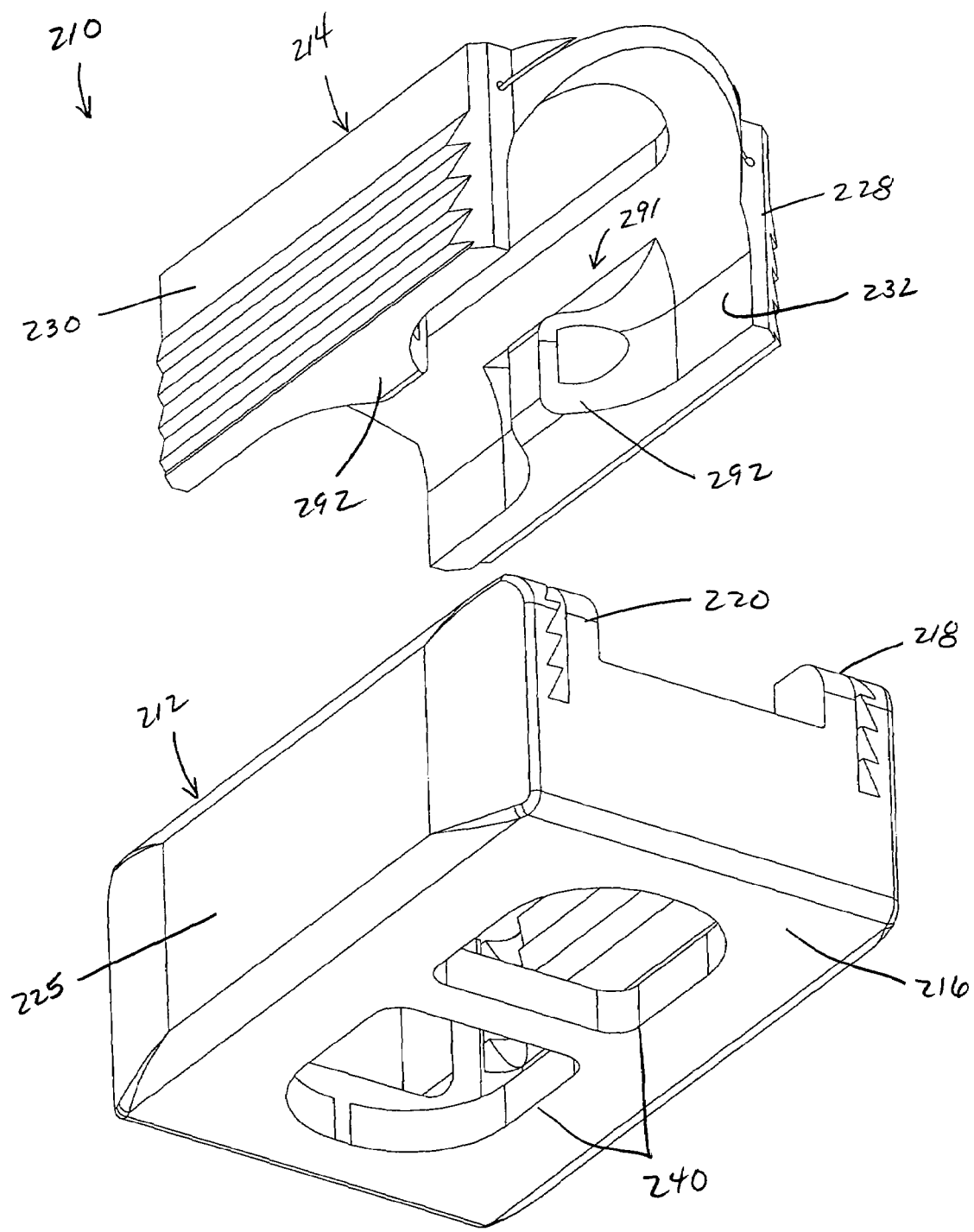
FIG. 7 is an exploded front perspective view of the implant of FIG. 6.
Figure 8:
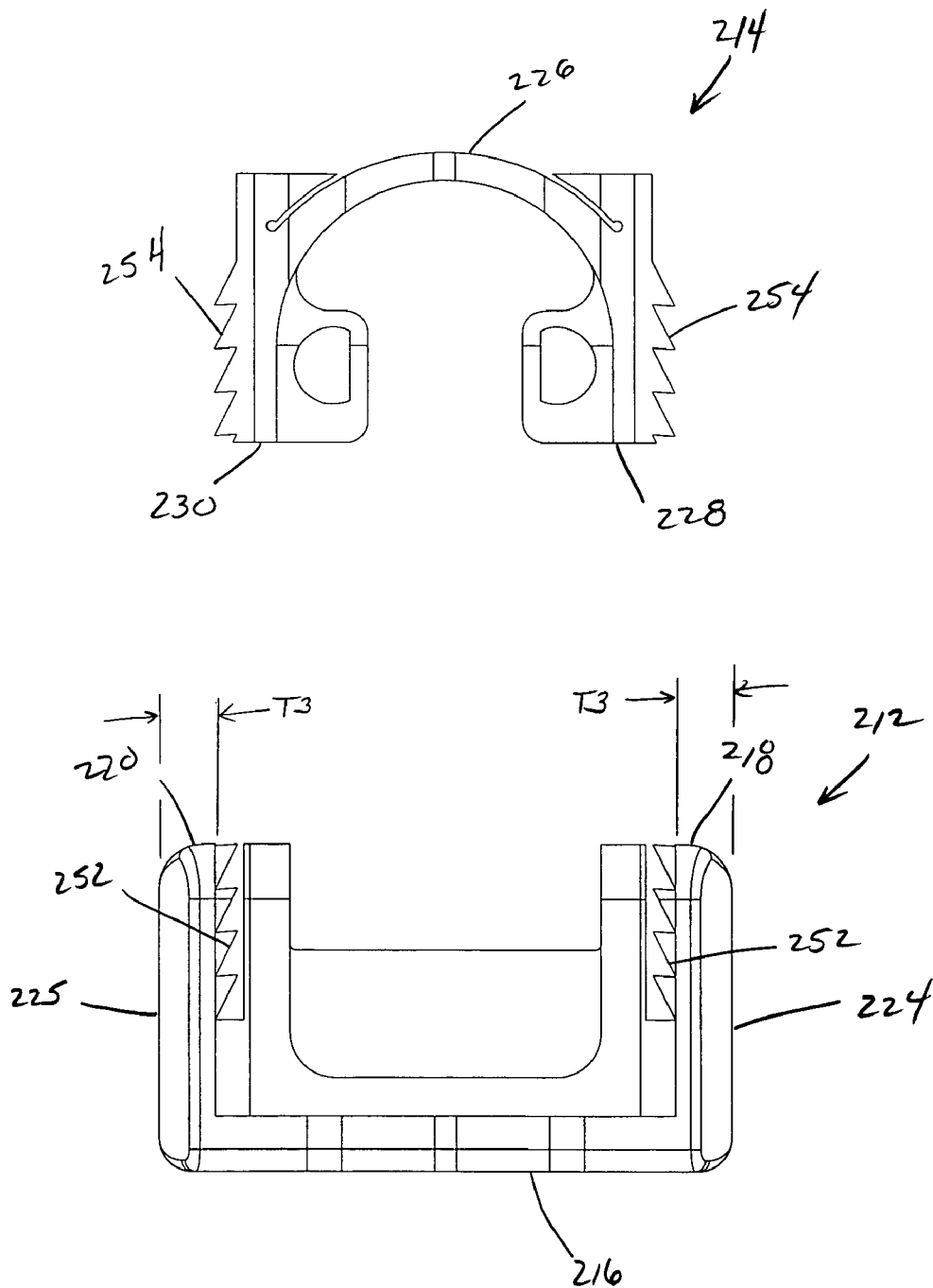
FIG. 8 is a front elevational view of the implant of FIG. 7.

The implant 10 illustrated in FIGS. 3–5 is only one embodiment of an implant employing the raked angle configuration of the locking arrangement. Referring now to FIGS. 6–8, an alternative embodiment of an expandable intervertebral implant 210 is illustrated. This implant embodiment 210 is similar to the previous embodiment including a first external member 212, a second internal member 214, and a locking arrangement 250 formed on the external and internal members 212, 214.

The internal member 214 includes a base portion 226 and first and second internal walls 228, 230. The base portion 226 defines a window 242 provided to encourage interlocking bone growth between vertebral elements V1, V2 (e.g. FIGS. 1 and 2). An implant handling arrangement 291, including implant handling structures 292, is formed on inside wall surfaces 232, 233 of the internal walls 228, 230 of the interior member 214.

The external member 212 includes a base portion 216 and first and second external walls 218, 220. The base portion 216 also defines at least one window 240 provided to encourage interlocking bone growth between vertebral elements V1, V2 (e.g. FIGS. 1 and 2). The external member 212 of this embodiment, however, does not include a ledge structure (70). Rather, the first and second walls 218, 220 of the external member 212 have an outer surface 224, 225 with a convex configuration. The convex outer surfaces 224, 225 increase the wall thickness T3 (FIG. 8) of each of the external walls 218, 220 to provide a more rigid construction to prevent lateral displacement or flexure of the walls 218, 220. A variety of structural configuration can be used to increase the wall thickness T3 and rigidity of the external member 212. In the illustrated embodiment, the convex outer surfaces 224 are generally tray-shaped.

The locking arrangement 250 of this implant embodiment 210 includes first and second interlocking teeth structures 252, 254 formed on each of the external and internal members 212, 214. The first and second interlocking teeth structures 252, 254 are similar to, and provide the same advantages as, the locking arrangement 50 previously described with respect to the first embodiment. That is, the locking arrangement 250 includes the raked angled teeth configurations 256, 258 described in FIGS. 11 and 12.

Figure 9:
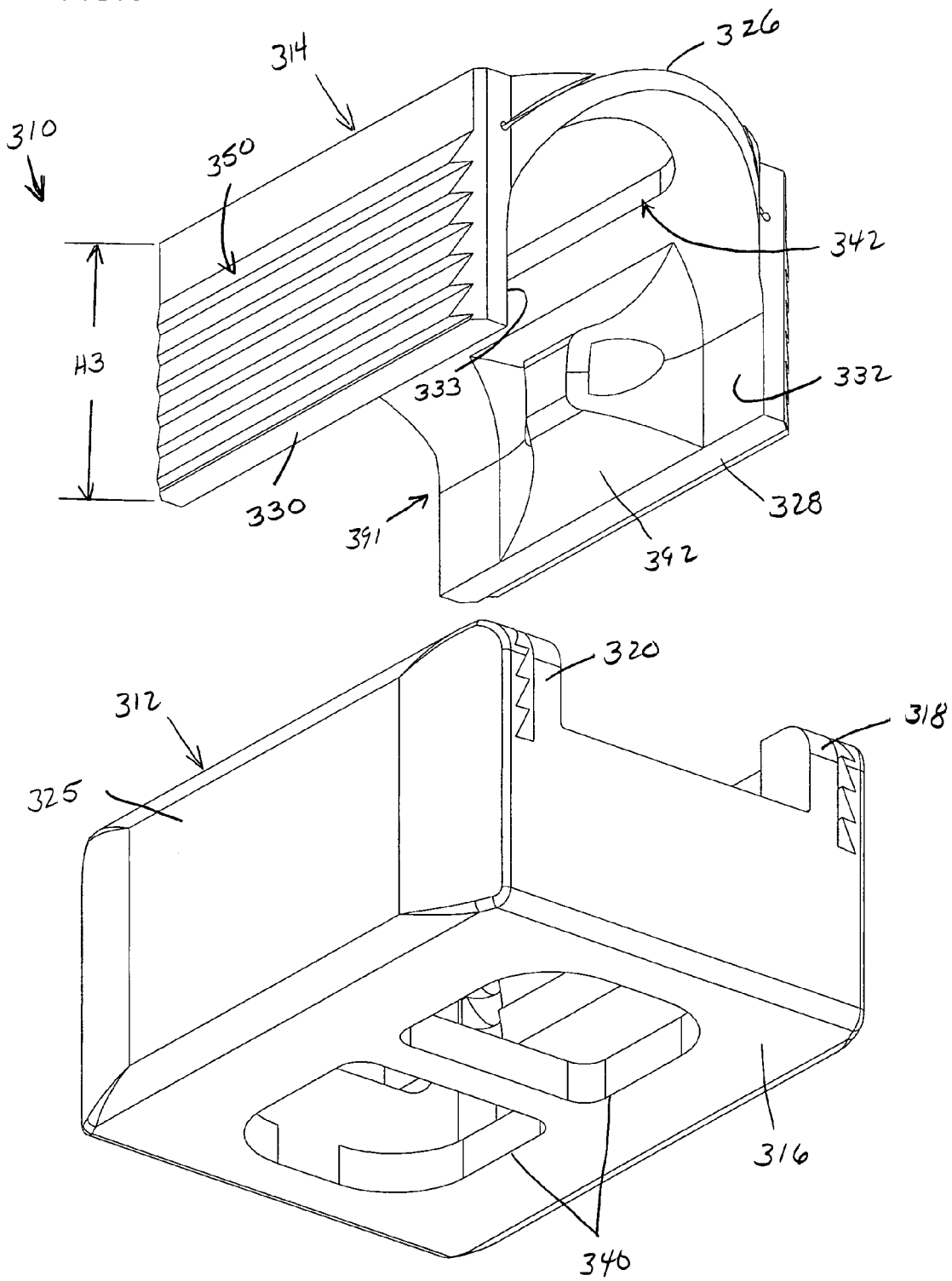
FIG. 9 is an exploded front perspective view of yet another embodiment of an expandable intervertebral implant according to the principles of the present disclosure.

Referring now to FIGS. 9 and 10, yet another alternative embodiment of an expandable intervertebral implant 310 is illustrated. In this embodiment, the implant 310 also includes a first external member 312, a second internal member 314, and a locking arrangement 350 formed on the external and internal members 312, 314.

The internal member 314 includes a base portion 326 and first and second internal walls 328, 330. The base portion 326 defines a window 342 provided to encourage interlocking bone growth between vertebral elements V1, V2 (e.g. FIGS. 1 and 2). An implant handling arrangement 391, including implant handling structures 392, is formed on inside wall surfaces 332, 333 of the internal walls 328, 330 of the interior member 314.

The external member 312 includes a base portion 316 and first and second internal walls 318, 320. The base portion 316 also defines at least one window 340 provided to encourage interlocking bone growth between vertebral elements V1, V2 (e.g. FIGS. 1 and 2). The external member 312 includes convex outer surfaces, 324, 325.

In this embodiment, the locking arrangement 350 includes a first interlocking teeth structure 352 (FIG. 10) formed on the first and second walls 318, 320 of the external member 312, and a corresponding second interlocking teeth structure 354 formed on the first and second walls 328, 330 of the internal member 314.

The second interlocking teeth structure 354 of the embodiment in FIG. 9 includes a greater number of teeth than in the previous embodiments (FIGS. 3–5 and 6–8). In particular, the first and second walls 328, 330 of the internal member 314 have a height H3 greater than that of the previous embodiments. In the illustrated embodiment, the height H3 is preferably about 0.45 inches and accommodates formation of about six individual teeth. The previous embodiment of FIGS. 3–5 and 6–8 have a height H2 that accommodates formation of about four teeth. This implant configuration 310 provides a surgeon with greater expansion capacity.

In use, the expandable intervertebral implant is used to space and separate two vertebral elements V1, V2. The installation procedure includes grasping the implant 10 with a surgical tool (not shown). At this point in the procedure, the external member 12 and the internal member 14 of the implant are assembled together and have a first non-expanded height. A variety of surgical tools can be used to grasp and handle the implant. In the illustrated embodiments, implant handling structures, e.g. 92, are provided. The implant handling structures 92 includes holes 94. The holes can be used such that a tool extends through the holes 94 to retain the implant. The implant is inserted between two vertebral elements V1, V2 in the non-expanded configuration having a first non-expanded height, as shown in FIG. 1. The implant is then ratcheted through a number of discrete incremental expansion positions to the expanded configuration having a second expanded height, as shown in FIG. 2. The implant can be expanded by forcibly separating the external member 12 and an internal member 14 in the direction of expansion (arrow B).

The implant 10 can be removed after installation and expansion, by disengaging the locking arrangement 50. In particular, the locking arrangement 50 can be disengaged by drawing or flexing the walls 28, 30 of the internal member 14 toward one another so that the second interlocking teeth structure 54 of the internal member 14 disengage from the first interlocking teeth structure 52 of the external member 12. Disengagement can be accomplished by inserting a surgical tool into the holes 94 of the implant handling structure 92, and squeezing the walls 28, 30 together, for example. When the first and second interlocking teeth structures 52, 54 have been disengaged, the compressive forces acting upon the external and internal members 12, 14 will compress the implant to the first non-expanded height. As can be understood, the second expanded height can be changed by disengaging the interlocking teeth structures 52, 54 and permitting the implant to ratchet to a reduced second height.

The above specification provides a complete description of the EXPANDABLE INTERVERTEBRAL IMPLANT CAGE. Since many embodiments of the invention can be made without departing from the spirit and scope of the invention, the invention resides in the claims hereinafter appended.

What is claimed is:

1. An expandable intervertebral implant, the implant comprising:
   a) an external member and an internal member; and
   b) an interlocking teeth structure formed on each of the external and internal members along which the external member and the internal member are adjustably engaged, the interlocking teeth structure arranged to permit expansion of the intervertebral implant along a direction of expansion, wherein:
   the internal member includes an internal base wall, first and second internal walls that extend from the internal base wall along a length of the base wall, wherein the first and second internal walls each have a free end and an attached end, the attached end connected to the base wall and the free end extending from the base wall in a generally perpendicular orientation;
   a flexible region in the internal member defined by a pair of slots formed adjacent to the attached ends of the first and second internal walls and extending along the length of the internal member base wall, wherein the flexible region provides for lateral displacement of the free ends of the first and second internal walls;
   the interlocking teeth structures formed on the external and internal members include external and internal engagement surfaces configured to engage one another to lock the implant in an expanded configuration against a compressive force applied to the internal and external members along a direction opposite the direction of expansion; and
   the external and internal engagement surfaces are arranged in a non-perpendicular orientation relative to the direction of implant expansion.

2. The implant of claim 1, wherein the internal member further comprises an end portion distal to the external member having an arcuate portion.

3. The implant of claim 2, wherein the internal member further comprises a shoulder portion having a surface generally perpendicular to the direction of expansion and recessed relative to at least part of the arcuate portion in the direction of expansion.

4. The implant of claim 3, wherein the internal member further comprises an additional shoulder portion having a surface generally perpendicular to the direction of expansion and recessed relative to at least part of the arcuate portion in the direction of expansion, the two shoulder portions disposed on opposite sides of the arcuate portion when viewed in the direction of expansion.

5. The implant of claim 3, wherein at least a portion of the arcuate portion and at least a portion of the shoulder portion define an arcuate gap therebetween.

6. The implant of claim 5, wherein the gap extends along a length of the shoulder to form the flexible region.

7. An expandable intervertebral implant, the implant comprising:
   a) an external member and an internal member, each of the members including a base and at least a first wall extending from the base along a length from a first end to a second end of the external and internal members; and
   b) an interlocking teeth structure formed on the first walls of each of the external and internal members, the interlocking teeth structures arranged to permit engagement of the external and internal members with each other along their respective first walls and permit expansion of the intervertebral implant along a direction of expansion;
   the interlocking teeth structure formed on the external member having an engagement surface that engages an engagement surface of the interlocking teeth structure formed on the internal member to lock the implant in an expanded configuration against a compressive force applied to the internal and external members along a direction opposite the direction of expansion; and the engagement surfaces of the interlocking teeth structures being arranged in a non-perpendicular orientation relative to the first walls of the external and internal members;

wherein the external member is a rigid construction configured to prevent flexure of the first wall of the external member; and wherein the internal member includes an arcuate slot positioned adjacent to an attached end of the first wall and extending from the first end to the second end of the internal member to form a flexible region within the internal member permitting flexure of a free end of the first and second walls of the internal member with respect to the base of the internal member.

8. The implant of claim 7, wherein the engagement surfaces of the interlocking teeth structure formed on the external member are raked upwardly about 4 degrees.

9. The implant of claim 8, wherein the engagement surfaces of the interlocking teeth structure formed on the internal member are raked downwardly about 4 degrees.

10. The implant of claim 7, wherein each of the engagement surfaces of the interlocking teeth structure formed on the internal and external members is angled approximately 94 degrees relative to the respective first wall.

11. The implant of claim 7, wherein the first walls of the external and internal members have an inside wall surface and an outside wall surface, the interlocking teeth structure being formed only on the inside wall surface of the external member, and only on the outside wall surface of the internal member.

12. The implant of claim 7, wherein the first wall of the internal member is positioned within the first wall of the external member, wherein the flexible region allows the interlocking teeth structure formed on the first wall of the internal member to flex toward the first wall of the external member.

13. The implant of claim 7, wherein the first wall of the internal member positioned within the first wall of the external member, wherein the flexible region allows the interlocking teeth structure formed on the first wall of the internal member to flex away from the first wall of the external member during expansion of the intervertebral implant.

14. The implant of claim 7, wherein the first wall of the external member has an external wall thickness, the external wall thickness being greater than an internal wall thickness of the internal member, wherein the external wall thickness of the external member prevents flexure of the first external wall.

15. An expandable intervertebral implant, the implant comprising:
 a) an external member including:
  i) a external base wall, and first and second external walls extending from the external base wall, the first and second external walls having a thickness to resist lateral displacement;
 b) an internal member coupled to the external member including:
  i) an internal base wall, and first and second internal walls extending from the internal base wall along a length of the base wall; wherein the first and second internal walls each have a free end and an attached end, the attached end connected to the internal base wall and the free end extending from the base wall in a generally perpendicular orientation
  ii) a flexible region in the internal member defined by a pair of slots formed adjacent to the attached ends of the first and second internal walls and extending along the length of the internal member base wall, wherein the flexible region provides for lateral displacement of the free ends of the first and second internal walls wherein the internal member is positioned with respect to the external member so that the first and second internal walls are engaged with and positioned within the first and second external walls;

c) a locking arrangement configured to lock the implant in an expanded position, the locking arrangement including:
  i) a first configuration of teeth formed on each of the first and second external walls, the first configuration of teeth being raked in an upwardly direction; and
  ii) a second configuration of teeth formed on each of the first and second internal walls, the second configuration of teeth being raked in a downwardly direction;
  wherein the first and second configurations of teeth defied the internal walls of the internal member about the flexible region toward the external walls of the external member when compressive forces are applied to the base walls of the external and internal members.

16. The implant of claim 15, wherein each of the upwardly and downwardly raked configuration of teeth of the external and internal members have a rake angle of between 1 degree and 8 degrees relative to the first and second walls of the external and internal members.

17. The implant of claim 15, wherein the first upwardly raked configuration of teeth are angled approximately 4 degrees relative to the first and second external walls of the external member.

18. The implant of claim 15, wherein the second downwardly raked configuration of teeth are angled approximately 4 degrees relative to the first and second internal walls of the internal member.

19. An expandable intervertebral implant, the implant comprising:
 a) a first member having a first base portion and walls extending from the first base portion;
 b) a second member having a second base portion, walls extending from the second base portion along a length of the second member base wall, and arcuate slots positioned adjacent the walls extending along the length of the second member, the arcuate slots defining a flexible region between each of the walls and the second base portion;
 c) an interlocking structure formed on each of the first and second members, the interlocking structure being configured to secure the implant in an expanded configuration;
 wherein the walls of the second member flex toward the walls of the first member when compressive forces are applied to the base portions of the first and second members.

20. The implant of claim 19, wherein the interlocking structure include ratchet teeth configured to permit linear expansion from a non-expanded configuration to the expanded configuration.

21. The implant of claim 20, wherein only the walls of the second member are configured to ratchet during expansion, and only the walls of the second member are configured to flex when compressive forces are applied to the base portions of the first and second members.

* * * * *

UNITED STATES PATENT AND TRADEMARK OFFICE
CERTIFICATE OF CORRECTION

PATENT NO. : 7,094,257 B2
APPLICATION NO. : 10/685767
DATED : August 22, 2006
INVENTOR(S) : James R. Mujwid It is certified that error appears in the above-identified patent and that said Letters Patent is hereby corrected as shown below:

In column 1, line 36, change "recent invertebral implants" to --recent intervertebral implants--.

In column 1, line 38, change "One such invertebral implant" to --One such intervertebral implant--.

In column 1, line 65, change "expandable invertebral implant" to --expandable intervertebral implant--.

In column 2, line 24, change "first configuration of teeth are raked" to --first configuration of teeth is raked--.

In column 2, line 25, change "second configuration of teeth are raked" to --second configuration of teeth is raked--.

In column 2, line 47, change "FIG. 1 is front elevational view" to --FIG. 1 is a front elevational view--.

In column 2, line 49, change "present disclosure," to --present disclosure;--.

In column 3, line 7, change "according the principles" to --according to the principles--.

In column 4, line 13, change "0.3 and 0.7 inches;" to --0.3 and 0.7 inch;--.

In column 4, line 14, change "0.4 and 0.6 inches;" to --0.4 and 0.6 inch;--.

In column 4, line 15, change "is about 0.5 inches." to --is about 0.5 inch;--.

In column 4, line 18, change "0.2 and 0.5 inches;" to --0.2 and 0.5 inch;--.

In column 4, line 19, change "0.2 and 0.4 inches;" to --0.2 and 0.4 inch;--.

In column 4, line 20, change "is about 0.3 inches." to --is about 0.3 inch.--.

In column 4, line 25, change "0.7 and 0.9 inches;" to --0.7 and 0.9 inch;--.

In column 4, line 26, change "is about 0.8 inches." to --is about 0.8 inch.--.

UNITED STATES PATENT AND TRADEMARK OFFICE
CERTIFICATE OF CORRECTION

PATENT NO. : 7,094,257 B2
APPLICATION NO. : 10/685767
DATED : August 22, 2006
INVENTOR(S) : James R. Mujwid It is certified that error appears in the above-identified patent and that said Letters Patent is hereby corrected as shown below:

In column 4, line 58, change "0.2 and 0.6 inches;" to --0.2 and 0.6 inch;--.

In column 4, line 59, change "0.3 and 0.5 inches;" to --0.3 and 0.5 inch;--.

In column 4, line 60, change "is about 0.4 inches." to --is about 0.4 inch.--.

In column 4, line 63, change "0.2 and 0.5 inches;" to --0.2 and 0.5 inch;--

In column 4, line 64, change "0.2 and 0.4 inches;" to --0.2 and 0.4 inch;--

In column 4, line 65, change "is about 0.3 inches." to --is about 0.3 inch.--.

In column 5, line 2, change "0.7 and 0.9 inches;" to --0.7 and 0.9 inch;--.

In column 5, line 3, change "is about 0.8 inches." to --is about 0.8 inch.--.

In column 5, line 23, change "The thickness T1 is design to" to --The thickness T1 is designed to--.

In column 6, line 44, change "meet the adjacent surface 78, 88" to --meet the adjacent surfaces 78, 88--.

In column 6, line 52, change "external member 12 are raked" to --external member 12 is raked--.

In column 6, line 54, change "internal member 14 are raked" to --internal member 14 is raked--.

In column 6, line 60, change "walls of the member 12, 14." to --walls of the members 12, 14.--.

In column 7, line 15, change "external member 12 is preferably" to --external member 12 are preferably--.

In column 7, line 21, change "the internal member 14 is preferably" to --the internal member 14 are preferably--.

In column 8, line 28, change "A variety of structural configuration" to --A variety of structural configurations--.

UNITED STATES PATENT AND TRADEMARK OFFICE
CERTIFICATE OF CORRECTION

PATENT NO. : 7,094,257 B2
APPLICATION NO. : 10/685767
DATED : August 22, 2006
INVENTOR(S) : James R. Mujwid It is certified that error appears in the above-identified patent and that said Letters Patent is hereby corrected as shown below:

In column 9, line 7, change "about 0.45 inches" to --about 0.45 inch--.

In column 9, line 9, change "embodiment of FIGS. 3-5 and 6-8 have" to --embodiments of FIGS. 3-5 and 6-8 have--.

In column 9, line 22, change "structures 92 includes holes 94." to --structures 92 include holes 94.--.

In column 9, line 38, change "structure 54 of the internal member 14 disengage" to --structure 54 of the internal member 14 disengages--.

In claim 13, column 11, line 38, change "internal member positioned within the first wall" to --internal member is positioned wihtin the first wall--.

In claim 15, column 11, line 63, change "perpendicular orientation" to --perpendicular orientation;--.

In claim 15, column 12, line 4, change "internal walls" to --internal walls; and--, as shown in the Amendment filed on April 3, 2006 on Page 6, claim 12, now claim 15.

In claim 15, column 12, line 8, change "second external wails;" to --second external walls;--, as shown in the Amendment filed on April 3, 2006 on Page 6, claim 12, now claim 15.

In claim 15, column 12, line 20, change "defied the internal walls" to --deflect the internal walls--, as shown in the Amendment filed on April 3, 2006 on Page 6, claim 12, now claim 15.

In claim 17, column 12, line 31, change "configuration of teeth are" to --configuration of teeth is--.

UNITED STATES PATENT AND TRADEMARK OFFICE
CERTIFICATE OF CORRECTION

PATENT NO.       : 7,094,257 B2
APPLICATION NO. : 10/685767
DATED            : August 22, 2006
INVENTOR(S)      : James R. Mujwid It is certified that error appears in the above-identified patent and that said Letters Patent is hereby corrected as shown below:

In claim 18, column 12, line 35, change "configuration of teeth are" to --configuration of teeth is--.

Signed and Sealed this

Twenty-seventh Day of February, 2007

JON W. DUDAS
*Director of the United States Patent and Trademark Office*